United States Patent
Ayral-Kaloustian et al.

(10) Patent No.: US 6,710,078 B2
(45) Date of Patent: Mar. 23, 2004

(54) 5-SUBSTITUTED-3(2H)-FURANONES USEFUL FOR INHIBITION OF FARNESYL-PROTEIN TRANSFERASE

(75) Inventors: Semiramis Ayral-Kaloustian, Tarrytown, NY (US); Irwin Hollander, Monsey, NY (US); Ann Aulabaugh, Ramsey, NJ (US)

(73) Assignee: Wyeth Holdings Corporation, Madison, NJ (US)

(*) Notice: Subject to any disclaimer, the term of this patent is extended or adjusted under 35 U.S.C. 154(b) by 0 days.

(21) Appl. No.: 10/226,792

(22) Filed: Aug. 23, 2002

(65) Prior Publication Data

US 2003/0073736 A1 Apr. 17, 2003

Related U.S. Application Data

(60) Provisional application No. 60/314,587, filed on Aug. 24, 2001.

(51) Int. Cl.⁷ .................. A61K 31/34; A61K 31/38; A61K 31/495; C07D 307/02; C07D 409/00
(52) U.S. Cl. .................. 514/474; 514/473; 514/471; 514/444; 514/255.05; 549/475; 549/60; 546/405
(58) Field of Search .................. 514/474, 473, 514/471, 444, 255.05; 549/475, 60; 546/405

(56) References Cited

U.S. PATENT DOCUMENTS

| | | | |
|---|---|---|---|
| 4,169,202 A | | 9/1979 | Jirkovsky et al. |
| 4,966,905 A | | 10/1990 | Felman et al. |
| 5,010,102 A | | 4/1991 | Felman et al. |
| 6,051,723 A | * | 4/2000 | Fischer et al. .............. 549/420 |
| 6,197,761 B1 | * | 3/2001 | Biggadike et al. .......... 514/174 |
| 6,239,173 B1 | * | 5/2001 | Wang et al. ................. 514/473 |
| 6,265,436 B1 | * | 7/2001 | Appere et al. .............. 514/473 |
| 6,333,346 B1 | * | 12/2001 | Menta et al. ............... 514/445 |
| 6,346,254 B1 | * | 2/2002 | Streicher et al. ........... 424/401 |
| 6,486,194 B2 | * | 11/2002 | Ducharme et al. ......... 514/438 |
| 6,492,416 B1 | * | 12/2002 | Shin et al. .................. 514/473 |
| 6,548,539 B1 | * | 4/2003 | Pikul et al. ................. 514/473 |
| 6,576,662 B2 | * | 6/2003 | Nanduri et al. ............. 514/473 |

OTHER PUBLICATIONS

G.L. Bolton, J.S. Sebolt–Leopold, J.C. Hodges; *Annu. Rep. Med. Chem.*, 1994, 29, 165.
R.J. A. Grand in "New Molecular Targets in Cancer Chemotherapy", J.D. Kerr and P. Workman, Eds. CRC Press, Boca Raton, FL., 1994, p. 97.
J.L. Bos, *Cancer Res.*, 1989, 49, 4682.
J.F. Hancock, H. Paterson, C.J. Marshall, *Cell*, 1990, 63, 133.
H.W. Park, S.R. Boduluri, J.F. Moomaw, P.J. Casey, L.S. Beese, *Science*, 1997, 275, 1800.
P.J. Casey, P.A. Solski, C.J. Der, J.E. Buss, *Proc. Natl. Acad. Sci. U.S.A*, 1989, 86, 8323.
S. Ayral–Kaloustian, J.S. Skotnicki, *Annu. Rep. Med Chem.*, 1996, 31, 171.

T.M. Williams, *Exp. Opin. Ther. Patents*, 1998, 8, 553.
SCH–66336, *Pharmaprojects*, 1998, No. 5128.
R–115777, *Pharmaprojects*, 1998, No. 5532.
Felman, S. W., et al., *J. Med. Chem.*, 1992, 35(7), 1183–89.
Smith, A. B., et al., *J. Amer. Chem. Soc.*, 103, 1501–13.
Baldwin, J.E., et al., *J. Amer. Chem. Soc.*, 1974, 96, 7125–7.
G.L. James, M.S. Brown, J.L. Goldstein, *Methods in Enzymology*, 1995, 255. 38–46.
M.A. Garcia, et al., *J. Biol. Chem.*, 1993, 268, 18415–18420.
J.F. Moomaw, P.J. Casey, *J. Biol. Chem.*, 1992, 267, 17438–17443.
P. Skehan, R. Storeng, D. Scudiero, A. Monks, J. Mcmohan, D. Vistica, J. Warren, J. Bokesh, S. Kenney, M.R. Boyd, *J. Natl. Cancer Instit.*, 1990, 82(13), 1107–1112.
L.V. Rubinstein, R.H. Shoemaker, K.D. Paull, R.M. Simon, S. Tosini, P. Skehan, D.A. Scudiero, A. Monks, M.R. Boyd, *J. Natl. Cancer Instit.*, 1990, 82(13), 1113–1118.
A. Monks, et al., *J. Natl. Cancer Instit.*, 1991, 83, 757–766.
M. R. Boyd, K.D. Paull., *Drug Development Res.*, 1995, 34, 91–109.
S.P. Fricker, R.G. Buckley, *Anticancer Research*, 1996, 16, 3755–3760.
John S. Wai, et al., "Synthesis and Biological Activity of Ras Farnesyl Protein Transferase Inhibitiors. Tetrapeptide Analogs with Amino Methyl and Carbon Linkages"; Bioorganic & Medicinal Chemistry, vol. 2, No. 9, 1994, pp. 939–947.
Samuel L. Graham, et al.; "Pseudopeptide Inhibitors of Ras Farnesyl–Protein Transferase", Journal of Medicinal Chemistry, vol. 37, No. 6, 1994, pp. 725–732.
Theresa M. Williams; "Inhibitors of Protein Farnesylation 1998", Expert Opinion on Therapeutic Patents, 1998, pp. 553–569.
Theresa M. Williams, et al.; "Farnesyl Transferase Inhibitors:Design of a New Class of Cancer Chemotherapeutic Agents", Advances in Medicinal Chemistry, vol. 4, 1999, pp. 273–314.
Martin Schlitzer, et al.; "Non–Prenylic Bisubstrate Farnesyltransferase Inhibitors. Part 3: Structural Requirements of the Central Moiety for Franesyltransferase Inhibitory Activity"; Bioorganic & Medicinal Chemistry, vol. 8, 2000, pp. 2399–2406.
US 10/226,792; PCT/US02/26674 PCT Search Report mailed Jan. 23, 2003.

* cited by examiner

*Primary Examiner*—Deborah C. Lambkin
(74) *Attorney, Agent, or Firm*—Daniel B. Moran

(57) ABSTRACT

Compounds of Formula (I):

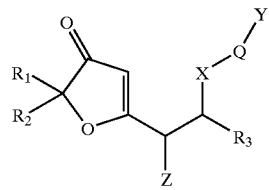

Formula (I)

wherein $R_1$, $R_2$, $R_3$, X, Y, Z and Q are as defined in the specification which compounds are inhibitors of Ras farnesyl-protein transferase enzyme (FPTase), and useful in treating ras oncogene-dependent tumors, such as cancers of the pancreas, colon, bladder, and thyroid and processes for the preparation of said compounds of Formula (I).

38 Claims, No Drawings

5-SUBSTITUTED-3(2H)-FURANONES USEFUL FOR INHIBITION OF FARNESYL-PROTEIN TRANSFERASE

"This application claims priority from provisional application Serial No. 60/314,587 filed on Aug. 24, 2001, now abandoned, the entire disclosure of which is hereby incorporated by reference."

FIELD OF THE INVENTION

The present invention relates to a novel series of 5-substituted-3(2H)-furanones, to pharmaceutical compositions containing them, to their use in cancer therapy and to a process for their preparation. The compounds inhibit Ras FPTase, and may be used as an alternative to, or in conjunction with, traditional cancer therapy for treating ras oncogene-dependent tumors, such as cancers of the pancreas, colon, bladder, and thyroid. Compounds in the invention may also be useful for controlling metastasis, suppressing angiogenesis, inducing apoptosis, and in treating Ras-associated proliferative diseases other than cancer, such as restenosis, neuro-fibromatosis, endometriosis, and psoriasis. These compounds may also inhibit prenylation of proteins other than Ras, and thus be effective in the treatment of diseases associated with other prenyl modifications of proteins.

BACKGROUND OF THE INVENTION

Mammalian H-, K-, and N-Ras proteins, encoded by H-, K-, and N-ras proto-oncogenes, respectively, are 21 kD GTP-binding proteins which possess intrinsic GTPase activity and play a fundamental role in cell proliferation and differentiation (G. L. Bolton, J. S. Sebolt-Leopold, and J. C. Hodges, Annu. Rep. Med. Chem., 1994, 29, 165; R. J. A. Grand in "New Molecular Targets in Cancer Chemotherapy" J. D. Kerr, and P. Workman, Eds., CRC Press, Boca Raton, Fla., 1994, p. 97). Specific mutations in the ras gene impair GTPase activity of Ras, leading to uninterrupted growth signals and to the transformation of normal cells into malignant phenotypes. Mutant ras oncogenes are found in approximately 25% of all human cancers, including 90% of pancreatic, 50% of colon, and 50% of thyroid tumors (J. L. Bos, Cancer Res., 1989, 49, 4682). It has been shown that normal cells transfected with mutant ras gene become cancerous and that unfarnesylated, cytosolic mutant Ras protein does not anchor in cell membranes and cannot induce this transformation (J. F. Hancock, H. Paterson, and C. J. Marshall, Cell, 1990, 63, 133). Posttranslational modification and plasma membrane association of mutant Ras is essential for this transforming activity. The first and required step in the processing of Ras is farnesylation at the cysteine residue of its carboxyl terminal motif, CAAX (C=Cys-186, A=aliphatic amino acid, X=usually methionine, serine or glutamine). Since its identification, the enzyme farnesyl-protein transferase (FPTase) that catalyzes this first processing step has emerged as a promising target for therapeutic intervention (H.-W. Park, S. R. Boduluri, J. F. Moomaw, P. J. Casey, and L. S. Beese, Science, 1997, 275, 1800; P. J. Casey, P. A. Solski, C. J. Der, and J. E. Buss, Proc. Natl. Acad. Sci. U.S.A., 1989, 86, 8323; S. Ayral-Kaloustian and J. S. Skotnicki, Annu. Rep. Med. Chem., 1996, 31, 165, and references therein). Major milestones have been achieved with small molecules, such as mimics of the tetrapeptide CAAX and analogs of farnesyl pyrophosphate, that show efficacy without toxicity in vitro as well as in mouse models bearing ras-dependent tumors or human xenografts with H-, N-, or K-ras mutations (S. Ayral-Kaloustian and J. S. Skotnicki, Annu. Rep. Med. Chem., 1996, 31, 165, and references therein; T. M. Williams, Exp. Opin. Ther. Patents, 1998, 8, 553, and references therein). Several low-molecular weight compounds that inhibit FPTase have entered Phase I trials in humans (SCH-66336, Pharmaprojects, 1998, No. 5128; R-115777, Pharmaprojects, 1998, No. 5532).

Accordingly, there is still a need for drugs for treating and preventing cancer. In particular, there is a need for drugs which inhibit or treat the growth of tumors expressing an activated Ras oncogene and which include cancers of the pancreas, colon, bladder and thyroid.

The present invention further provides a method of treatment of ras oncogene-dependent tumors, such as cancers of the pancreas, colon, bladder, and thyroid; a method of controlling metastasis, suppressing angiogenesis, and inducing apoptosis; a method of treating Ras-associated proliferative diseases other than cancer, such as restenosis, neuro-fibromatosis, endometriosis, and psoriasis. The compounds of the present invention may also inhibit prenylation of proteins other than Ras, and thus provide a method of treatment of diseases associated with other prenyl modifications of proteins.

BRIEF SUMMARY OF THE INVENTION

The present invention discloses compounds represented by Formula (I):

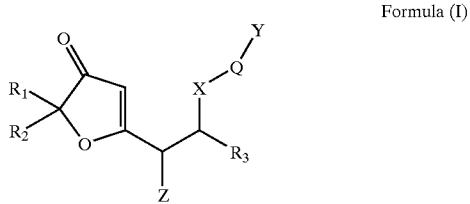

Formula (I)

wherein:
R$_1$ is alkyl of 1 to 10 carbon atoms optionally substituted with 1 to 4 substituents independently selected from the group consisting of alkyl of 1 to 10 carbon atoms, —OH, —SH, —NH$_2$, and halogen, alkenyl of 2 to 12 carbon atoms, optionally substituted aralkyl of 7 to 13 carbon atoms, optionally substituted aryl of 6 to 12 carbon atoms, and optionally substituted heteroaryl;

R$_2$ is phenyl, substituted phenyl (having from 1 to 3 substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms),or naphthyl;

R$_3$ is optionally substituted aryl and optionally substituted heteroaryl;

X is —O—, —S—, or —NH—;

Y is —OH, —SH, —SR$_4$, —NH$_2$, —NHR$_5$, —CO$_2$H, —CONHOH, halogen, or heteroaryl;

R$_4$ is hydrogen, alkyl of 1 to 10 carbon atoms, aryl of 6 to 12 carbon atoms, and aralkyl of 7 to 13 carbon atoms;

R$_5$ is alkyl of 1 to 10 carbon atoms, aryl of 6 to 12 carbon atoms, and aralkyl of 7 to 13 carbon atoms;

Z is H or methyl;

Q is an alkyl chain of 2 to 6 carbon atoms optionally substituted with 1 to 4 substituents selected from the group consisting of alkyl of 1 to 10 carbon atoms, —OH, —SH, —NH$_2$, halogen and alkenyl of 2 to 6 carbon atoms;

or a pharmacologically acceptable salt thereof.

Among the preferred groups of compounds of Formula (I) of this invention including pharmaceutically acceptable salts thereof are those in the subgroups below, wherein the other variables of Formula (I) in the subgroups are as defined above wherein:

a.) X is S;

b.) X is S;
Y is SH;

c.) X is S;
Y is SH;
R$_3$ is thienyl;

d.) X is S;
Y is SH, tetrazole or imidazole;
R$_3$ is thienyl;

e.) X is S;
Y is SH;
R$_2$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms;
R$_3$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms;

More preferred aspects of this invention includes compounds of Formula (I) including pharmaceutically acceptable salts thereof are those in the subgroups below, wherein the other variables of Formula (I) in the subgroups are as defined above wherein: X is S; Z is H or methyl; and R$_1$ is methyl;

a) R$_2$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms when R$_3$ is thienyl and Y is SH;

b) R$_2$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms when R$_3$ is thienyl and Y is pyrazine;

c) R$_2$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms;
R$_3$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms when Y is SH.

Specifically preferred compounds of this invention according to Formula (I) for treating or controlling ras oncogene-dependent tumors and associated proliferative diseases in warm-blooded animals preferably mammals, most preferably humans in need thereof are the following compounds or a pharmaceutically acceptable salt thereof:

5-(2-{[(2S*,3S*)-2,3-dihydroxy-4-mercaptobutyl]thio}-2-thien-3-ylethyl)-2-methyl-2-phenylfuran-3(2H)-one;

5-(2-{[(2R*,3S*)-2,3-dihydroxy-4-mercaptobutyl]thio}-2-thien-3-ylethyl)-2-methyl-2-phenylfuran-3(2H)-one;

5-[2-{[(2R,3R)-2,3-dihydroxy-4-mercaptobutyl]thio}-2-(3-thienyl)ethyl]-2-methyl-2-phenylfuran-3(2H)-one;

5-(2-{[(2S*,3S*)-2,3-dihydroxy-4-mercaptobutyl]thio}-2-thien-3-ylethyl)-2-(4-fluorophenyl)-2-methylfuran-3(2H)-one;

5-(2-{[(2R*,3S*)-2,3-dihydroxy-4-mercaptobutyl]thio}-2-thien-3-ylethyl)-2-(4-fluorophenyl)-2-methylfuran-3(2H)-one;

5-(2-{[(2R,3R)-2,3-dihydroxy-4-mercaptobutyl]thio}-2-thien-3-ylethyl)-2-(4-fluorophenyl)-2methylfuran-3(2H)-one;

5-[2-{[(2S*,3S*)-2,3-dihydroxy-4-mercaptobutyl]thio}-2-(2-nitrophenyl)ethyl]-2-methyl-2-phenylfuran-3(2H)-one;

5-(2-{[(2S*3S*)-2,3-dihydroxy-4-mercaptobutyl]thio}-1-methyl-2-thien-3ylethyl)-2-methyl-2-phenylfuran-3(2H)-one;

5-[2-(4-Mercapto-butylthio)-2-thiophen-3-yl-ethyl]-2-methyl-2-phenylfuran-3-one;

5-[2-[(4-hydroxybutyl)thio]-2-(3-theinyl)ethyl]-2-methyl-2-phenylfuran-3(2H)-one;

5-[2-[(3-mercaptopropyl)thio]-2-(3-thienyl)ethyl]-2-methyl-2-phenylfuran-3(2H)-one;

5-[2-[(5-mercaptopentyl)thio]-2-(3-thienyl)ethyl]-2-methyl-2-phenylfuran-3(2H)-one;

5-[2-[(2-mercaptoethyl)thio]-2-(3-thienyl)ethyl]-2-methyl-2-phenylfuran-3(2H)-one;

5-[2-[(3-hydroxy-2-mercaptopropyl)thio]-2-(3-thienyl)ethyl]-2-methyl-2-phenylfuran-3(2H)-one;

5-[2-[(3-hydroxypropyl)thio]-2-(3-thienyl)ethyl]-2-methyl-2phenylfuran-3(2H)-one;

5-[2-[(2,3-dihydroxypropyl)thio]-2-(3-thienyl)ethyl]-2-methyl-2-phenylfuran-3(2H)-one;

2-methyl-2-phenyl-5-[2-[(2-pyrazin-2-ylethyl)thio]-2-(3-thienyl)ethyl]furan-3(2H)-one;

5-[2-[(2-hydroxyethyl)thio]-2-(3-thienyl)ethyl]-2-methyl-2-phenylfuran-3(2H)-one;

2-(4-fluorophenyl)-5-[2-[(2-hydroxyethyl)thio]-2-(3-thienyl)ethyl]-2-methylfuran-3(2H)-one; and (2R)-2-amino-3-{[2-(5-methyl-4-oxo-5-phenyl-4,5-dihydrofuran-2-yl)-1-thien-3-ylethyl]thio}propanoic acid.

It is understood that the definition of compounds of Formula (I) when R$_1$, R$_2$, R$_3$, R$_4$, or R$_5$, contain asymmetric carbons, encompass all possible stereoisomers and mixtures thereof which possess the activity discussed below. In particular, the definition encompasses racemic modifications and any optical isomers which possess the indicated activity. Optical isomers may be obtained in pure form by standard separation techniques or enantiomer specific synthesis. It is understood that this invention encompasses all crystalline forms of compounds of Formula (I). The pharmaceutically acceptable salts of the basic compounds of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic, and similarly known acceptable acids. Where $R_1$, $R_2$, $R_3$, $R_4$, $R_5$ or Y contains a carboxyl group, salts of the compounds in this invention may be formed with bases such as alkali metals (Na, K, Li) or alkaline earth metals (Ca or Mg).

For the compounds of Formula (I) defined above and referred to herein, unless otherwise noted, the following terms are defined: Halogen, as used herein means chloro, fluoro, bromo and iodo.

Alkyl as used herein means a branched or straight chain having from 1 to 10 carbon atoms and more preferably from 1 to 6 carbon atoms. Exemplary alkyl groups include methyl, ethyl, propyl, isopropyl, butyl, isobutyl, t-butyl, pentyl and hexyl.

Alkenyl as used herein means a branched or straight chain having from 2 to 12 carbon atoms and more preferably from 2 to 6 carbon atoms, the chain containing at least one carbon-carbon double bond and all possible configurational isomers. Alkenyl, may be used synonymously with the term olefin and includes alkyldienes. Exemplary alkenyl groups include ethylene, propylene, isobutylene, ethenyl, 3-hexen-1-yl and the like optionally substituted with phenyl, phenyl optionally substituted with one to three substituents independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms.

Aryl as used herein means a mono or bicyclic aromatic radical, having 6 to 12 carbon atoms. Preferred aryl groups include phenyl, alpha-naphthyl and beta-naphthyl and the like optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms.

Aralkyl as used herein means an aryl-alkyl group in which the aryl and alkyl group are previously defined. Exemplary aralkyl groups include benzyl and phenethyl.

Alkoxy as used herein means an —O-alkyl group in which the alkyl group is as previously described. Exemplary alkoxy groups include methoxy, ethoxy, n-propoxy, i-propoxy, n-butoxy, and t-butoxy.

Heteroaryl denotes an unsubstituted or optionally substituted monocyclic 5 or 6 membered ring, which contains 1 to 4, or particularly 1 or 2 heteroatoms which may be the same or different. Nitrogen, oxygen and sulfur are the preferred heteroatoms, provided that the heteroaryl does not contain O—O, S—S or S—O bonds. Specific examples include 2-thienyl, 3-thienyl, furan, pyrrole, pyrazole, imidazole, 1,2,3-triazole, 1,2,4-triazole, tetrazole, thiazole, isoxazole, 1,3,4-oxadiazole, 1,2,4-oxadiazole, 1,3,4-thiadiazole, pyridine, pyrimidine, pyrazine, pyridazine and 1,3,5-triazine. The heteroaryl ring may be oxidized when a heteroatom is a nitrogen atom to provide the corresponding N-oxide, including pyridine-N-oxide. The heteroaryl ring may be oxidized on a sulfur atom to provide the corresponding sulfoxide or sulfone, including thiophene-1-oxide.

Phenyl as used herein refers to a 6-membered aromatic ring.

A group, e.g. phenyl, aryl, heteroaryl, described as optionally substituted, unless otherwise provided for, denotes that when substituted has from 1 to 3 substituents said substituents being for example each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms.

Where terms are used in combination, the definition for each individual part of the combination applies unless defined otherwise. For instance, aralkyl refers to an aryl group, and alkyl refers to the alkyl group as defined above.

Additionally, this invention provides a method of treatment, by administration of an effective amount of compounds of Formula (I), of ras oncogene-dependent tumors, which include cancers of the pancreas, colon, bladder, and thyroid; a method of controlling metastasis, suppressing angiogenesis, and inducing apoptosis; a method of treating Ras-associated proliferative diseases other than cancer, which include restenosis, neuro-fibromatosis, endometriosis, and psoriasis. The compounds of Formula (I) may also inhibit prenylation of proteins other than Ras, and thus provide a method of treatment of diseases associated with other prenyl modifications of proteins.

The compounds of Formula (I) inhibit farnesyl-protein transferase and the farnesylation of the oncogene protein Ras. Thus, this invention further provides a method of inhibiting farnesyl protein transferase, (e.g., Ras farnesyl protein transferase) in mammals, especially humans, by the administration of an effective amount of the compounds of Formula (I). The administration of the compounds of this invention to patients, to inhibit farnesyl protein transferase, is useful in the treatment of the cancers and other diseases described below.

This invention provides a method for inhibiting or treating the abnormal growth of cells, including transformed cells by administering an effective amount of a compound of Formula (I). Abnormal growth of cells refers to cell growth independent of normal regulatory mechanisms (e.g., loss of contact inhibition). This includes abnormal growth of tumor cells (tumors) expressing an activated Ras oncogene; tumor cells in which the Ras protein is activated as a result of oncogenic mutation in another gene; and benign and malignant cells of other proliferative diseases in which aberrant Ras activation occurs.

This invention also provides a method for inhibiting or treating tumor growth by administering an effective amount of a compound of Formula (I), described herein, to a mammal (e.g., a human) in need of such treatment. In particular, this invention provides a method for inhibiting or treating the growth of tumors expressing an activated Ras oncogene by administration of an effective amount of a compound of Formula (I). Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancer and prostate cancer.

In another aspect, this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form-with said inhibition or treatment being accomplished by the administration of an effective amount of a compound of Formula (I), to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the compounds of Formula (I).

Additionally, this invention provides a method of inhibition or treating the abnormal growth of cells, by administration of an effective amount of compounds of Formula (I), of ras-oncogene-dependent tumors, which tumors include cancers of the pancreas, colon, bladder, and thyroid in a mammal in need thereof. Without wishing to be bound by theory, these compounds may function through the inhibition of G-protein function, such as ras p21, by blocking G-protein isoprenylation, thus making them useful in the treatment of proliferative diseases such as tumor growth and cancer. Without wishing to be bound by theory, compounds of Formula (I) inhibit Ras farnesyl-protein transferase, and thus antiproliferative activity of ras-transformed cells and other prenyl modifications of proteins.

In another aspect, the invention provides a process for the preparation of a compound of Formula (I)

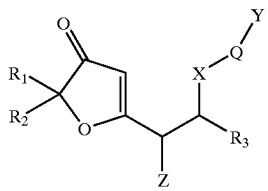

Formula (I)

wherein:
- $R_1$ is alkyl of 1 to 10 carbon atoms optionally substituted with 1 to 4 substituents selected from the group consisting of alkyl of 1 to 10 carbon atoms, —OH, —SH, —NH$_2$, and halogen, alkenyl of 2 to 12 carbon atoms, optionally substituted aralkyl of 7 to 13 carbon atoms, optionally substituted aryl of 6 to 12 carbon atoms, and optionally substituted hereroaryl;
- $R_2$ is phenyl, substituted phenyl (having from 1 to 3 substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms), or naphthyl;
- $R_3$ is optionally substituted aryl and optionally substituted heteroaryl;
- X is —O—, —S—, or —NH—;
- Y is —OH, —SH, —SR$_4$, —NH$_2$, —NHR$_5$, —CO$_2$H, —CONHOH, halogen, or heteroaryl;
- $R_4$ is hydrogen, alkyl of 1 to 10 carbon atoms, aryl of 6 to 12 carbon atoms, and aralkyl of 7 to 13 carbon atoms;
- $R_5$ is alkyl of 1 to 10 carbon atoms, aryl of 6 to 12 carbon atoms, and aralkyl of 7 to 13 carbon atoms;
- Z is H or methyl;
- Q is an alkyl chain of 2 to 6 carbon atoms optionally substituted with 1 to 4 substituents selected from the group consisting of alkyl of 1 to 10 carbon atoms, —OH, —SH, —NH$_2$, halogen and alkenyl of 2 to 6 carbon atoms;

or a pharmacologically acceptable salt thereof which comprises (a) reacting a compound of the formula

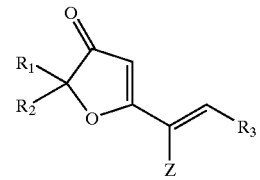

with a compound of the formula HX—Q—Y to give a compound of Formula (I);

(b) optionally converting a compound of Formula (I) to a pharmaceutically acceptable salt thereof.

DETAILED DESCRIPTION OF THE INVENTION

Compounds of this invention were prepared via 1,6-conjugate addition reactions, according to Scheme I. Intermediates 1 were synthesized according to the procedures described in U.S. Pat. Nos. 5,010,102 and 4,966,905 and 4,169,202 incorporated herein by reference or commercially available. Further procedures for the synthesis of intermediate compounds 1 of the invention are described in Felman, S. W., et al., J. Med. Chem. 1992, 35 (7), 1183–89. In addition, intermediates 1 can be synthesized using a combination of procedures described in Smith, A. B., et al., J. Amer. Chem. Soc., 1981, 103, 1501–13, and Baldwin, J. E., et al., J. Amer. Chem. Soc., 1974, 96, 7125–7. Intermediates 2 are commercially available compounds, or may be synthesized by standard literature procedures. Methods A–C may be used to prepare compounds of Formula (I) as described in Scheme I. Referring to Method A, as described in Scheme I, intermediate 1 where $R_1$, $R_2$, $R_3$ and Z are hereinbefore defined was stirred at room temperature for 10 to 24 hours, with intermediate 2 where X, Q and Y are hereinbefore defined in the presence of triethylamine (TEA) in tetrahydrofuran (THF) to afford compounds of Formula (I). Referring to Method B, as described in Scheme I, intermediate 1 where $R_1$, $R_2$, $R_3$ and Z are hereinbefore defined was stirred at room temperature for 10 to 24 hours, with intermediate 2 where X, Q and Y are hereinbefore defined in the presence of aqueous phosphate buffer (pH 7.5) and in the presence of an organic co-solvent such as ethyl alcohol (EtOH) or acetonitrile to afford compounds of Formula (I). Alternatively, using Method C, intermediate 1 where $R_1$, $R_2$, $R_3$ and Z are hereinbefore defined was stirred at room temperature for 10 to 24 hours, with intermediate 2 where X, Q and Y are hereinbefore defined in the presence of 0.05M Tris/HCl (tris(hydroxymethyl)aminomethane hydrochloride) in dimethylsulfoxide (DMSO)for 10 to 24 hours to afford compounds of Formula (I).

Scheme I

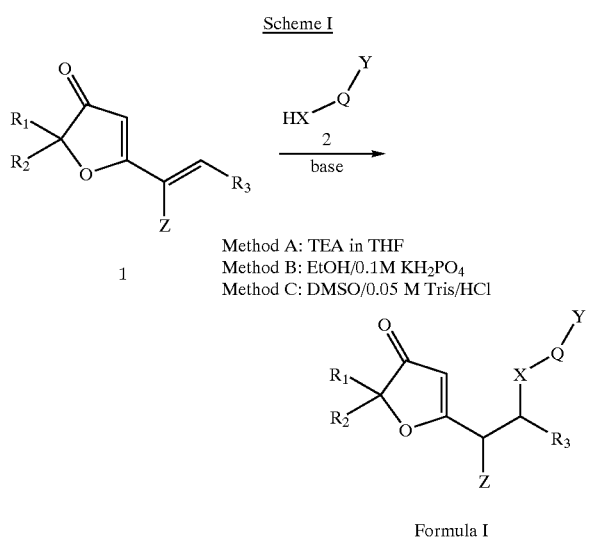

Method A: TEA in THF
Method B: EtOH/0.1M KH$_2$PO$_4$
Method C: DMSO/0.05 M Tris/HCl Formula I

STANDARD PHARMACOLOGICAL TEST PROCEDURES

The ability of the compounds of this invention to inhibit FPTase was evaluated in the standard pharmacological in vitro test procedures described below. Data for representative examples is summarized in Table I.

Enzyme test procedure: FPTase inhibition in vitro assay was performed according to James, G. L., Brown, M. S., and Goldstein, J. L., *Methods in Enzymology*, 1995, 255, 38–46; and Garcia, M. A., et al., *J. Biol. Chem.*, 1993, 268, 18415–18420.

Materials—Purified FPTase (Moomaw, J. F. and Casey, P. J., *J. Biol. Chem.*, 1992, 267,17438–17443), purified His$_6$-Ras, inhibitor compounds at 10 mg/ml or 10 mM in 100% DMSO, $^3$H-FPP (50,000 dpm/pmol) Amersham, TCA/SDS (6%/2%), TCA (6%), Glass fiber filters (0.22–0.45 m), vacuum manifold or 96 well filtration plates.

Methods—1. Dilute FPTase inhibitors from stock solutions to 2.5× in 2.5% DMSO, 10 mM DTT, 0.5% octyl-B-glucoside. 2. Solution #1 is added to FPTase reaction in a volume of 20 ml. 3. Standard reaction mix, 50 ml, contains 50 mM Tris (7.5),10 mM ZnCl$_2$, 3 mM MgCl$_2$, 20 mM KCl, 5 mM DTT, 0.2% octyl-B-glucoside, 1% DMSO, 40 mM His$_6$-Ras, 10 ng FPTase, and various concentrations of FPTase inhibitors. 4. Incubate for 30–90 min at 25° C. 5. Stop reactions with TCA/SDS (6%/2%), hold at 4° C. for 45–60 min. 6. Filter by manifold or 96 well plate, wash filter 3–5× with TCA (6%). 7. Add scintillant to filters, measure $^3$H-FPP incorporation into Ras protein.

Analysis of Results—Percent inhibition by test compounds is determined by the following:

(cpm from precipitated Ras with test compounds)−(background cpm)×100=% inhibition.

(cpm from precipitated Ras without test compounds)−(background cpm)

Cell-based test procedure: Tumor inhibition in vitro assay was performed according to P. Skehan, R. Storeng, D. Scudiero, A. Monks, J. McMohan, D. Vistica, J. Warren, H. Bokesh, S. Kenney, and M. R. Boyd, *J. Natl. Cancer Instit.*, 1990, 82 (13), 1107–1112; L. V. Rubinstein, R. H. Shoemaker, K. D. Paull, R. M. Simon, S. Tosini, P. Skehan, D. A. Scudiero, A. Monks, and M. R. Boyd, *J. Natl. Cancer Instit.*, 1990, 82 (13), 1113–1118; A. Monks, et al., *J. Natl. Cancer Instit*, 1991, 83, 757–766; M. R. Boyd and K. D. Paull, *Drug Development Res.*, 1995, 34, 91–109; and S. P. Fricker and R. G. Buckley, *Anticancer Research*, 1996, 16, 3755–3760.

Materials—Cell Lines: Human tumor cell lines LS174T, HTB39, LoVo and CaCo2. Cell Media: RPMI 1640 (or DMEM medium and McCoy's medium) with 10% Fetal Bovine Serum supplemented with L-glutamine and Pennicilin/Streptomycin. Compounds: Supplied usually as a 10 mM stock in 100% DMSO. Normal Saline: 150 mM NaCl Trichloroacetic Acid (TCA): 50% (w/v) in water. Sulforhodamine (SRB): 0.4% (w/v) in 1% Acetic Acid. Tris Base: 10 mM in water.

Methods—Cells are plated at 2000 cells per well, per 200 μl media, and allowed to adhere overnight at 37° C. At 24 h post plating, compounds are added directly at a volume of 0.5 μl. Compound is first diluted in DMSO to generate concentrations of compound or reference standard of: 1, 5, 10 and 25 μM. Dilutions can be made in an identical 96 well plate so that compounds can be added using a multichannel micropipettor set at 0.5 μl. The cells are then incubated for four days after which the media is removed using a 12 well manifold by first tipping the plate forward at a 45 degree angle and then inserting the manifold in an upright orientation to prevent the tips of the manifold from disturbing cells at the bottom of the plate. 200 μl of normal saline is then added to each well using an 8 well multichannel pipettor, followed by the careful addition of 50 μl of 50% TCA. The plates are then incubated for 2 h at 4° C., after which the supernatant is removed using the same technique as above and the plates washed twice with 200 μl water. The plates are then air dried and 50 μl of SRB stock solution is carefully added so that the entire bottom of each well is covered. This again can be used using an 8 well multichannel pipettor. The SRB is incubated with fixed cells for 15 min at room temperature, after which the SRB is removed with the manifold as described above and the plates washed twice with 350 μl of 1% acetic acid per well each time. The plates are then air dried after which the bound SRB is released from protein by the addition of 200 μl of Tris base. Resolubilizing the SRB is aided by placing the plates on a rotator for 15–30 min. The absorbance of each well is determined at 550 or 562 nm using a microtiter plate reader.

Analysis of Results—Each compound or dilution thereof is performed in triplicate. Outliers are identified by visual inspection of the data. Each plate should have a control (vehicle only). A standard curve is constructed by plotting the concentration of compound against the average absorbance calculated at that concentration. A curve is plotted and the concentration at which the curve passes through the 50% absorbance mark seen in the control well is the IC$_{50}$ calculated for that compound.

TABLE I

| | in vitro FTase Inhibition Assay | |
|---|---|---|
| Example # | IC$_{50}$ (vs. H-Ras) μM | IC$_{50}$ (vs. K-Ras) μM |
| 1 | 0.06 | 0.10 |
| 2 | 0.19 | |
| 3 | 0.18 | |
| 6 | 0.12 | 0.14 |

TABLE I-continued

| | in vitro FTase Inhibition Assay | |
|---|---|---|
| Example # | $IC_{50}$ (vs. H-Ras) $\mu M$ | $IC_{50}$ (vs. K-Ras) $\mu M$ |
| 7 | 0.32 | 0.09 |
| 8 | 0.50 | 0.70 |
| 9 | 1.5 | 3.7 |
| 10 | 5.5 | >10 |
| 11 | 0.06 | 0.15 |
| 12 | 8 | |
| 13 | 0.18 | 1 |
| 14 | 7.2 | 4.5 |
| 15 | 8.3 | |
| 16 | 5 | |
| 17 | >10 | >10 |
| 18 | 0.55 | |
| 19 | >10 | |
| 20 | >10 | |

*H-Ras or K-Ras used as substrates for farnesylation

Compounds of this invention were tested in cell-based assays against human tumor cell lines LS174T, HTB39 and LoVo, as described under Assays. The range observed for inhibition of cell growth was $IC_{50}$=5 to >25 $\mu M$.

Based on the results of these standard pharmacological test procedures, the compounds of this invention are useful as agents for treating, inhibiting or controlling ras-associated diseases by inhibiting farnesyl-protein transferase enzyme, when administered in amounts ranging from about 1 to about 200 mg/kg of body weight per day. A preferred regimen for optimum results would be from about 1 mg to about 100 mg/kg of body weight per day and such dosage units are employed that a total of from about 100 mg to about 1000 mg of the active compound for a subject of about 70 kg of body weight are administered in a 24 hour period.

The dosage regimen for treating mammals may be adjusted to provide the optimum therapeutic response. For example, several divided doses may be administered daily or the dose may be proportionally reduced as indicated by the exigencies of the therapeutic situation. A decidedly practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between 10 and 1000 mg of active compound. The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures therof in oils. Under ordinary conditions of storage and use, these preparations contain a preservative to prevent the growth or microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and starage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

The present invention accordingly provides a pharmaceutical composition which comprises a compound of Formula (I) of this invention in combination or association with a pharmaceutically acceptable carrier. In particular, the present invention provides a pharmaceutical composition which comprises an effective amount of a compound of this invention and a pharmaceutically acceptable carrier.

As used in accordance with this invention, the term providing an effective amount of a compound means either directly administering such compound, or administering a prodrug, derivative, or analog which will form an effective amount of the compound within the body.

The invention will be more fully described in conjunction with the following specific examples which are not to be construed as limiting the scope of the invention.

EXAMPLE 1

5-(2-{[(2S*,3S*)-2,3-Dihydroxy-4-mercaptobutyl] thio}-2-thien-3-ylethyl)-2-methyl-2-phenylfuran-3 (2H)-one Method A. A solution of (E)-2-methyl-2-phenyl-5-[2-(3-thienyl)ethenyl]-3(2H)-furanone (52 mg, 0.18 mmol) in anhydrous THF (1.5 mL) was treated with 1,4-dithio-DL-threitol (78 mg, 0.50 mmol) and TEA (77.5 µL, 0.55 mmol), at room temperature, under nitrogen atmosphere. After 24 h at ambient temperature, the mixture was taken up in ether and washed with brine. The organic layer was dried and concentrated to give a crude oil (112 mg), which was purified by flash column chromatography (1:1,5 EtOAc/ hexane) and identified as 5-(2-{[(2S*,3S*)-2,3-dihydroxy-4-meracaptobutyl]thio}-2-thien-3-ylethyl)-2-methyl-2-phenylfuran-3(2H)-one (42.2 mg, 54%) consisting of a mixture of diastereomers: $^1$H NMR (CDCl$_3$) δ1.43 (m, 1H), 1.66, 1.68 and 1.72 (overlapped singlets, 3H), 2.40–2.70 (m, 4H), 3.10–3.25 (m, 2H), 3.40–3.75 (two broad s, fine structure, 2H), 4.48 (m, 1H), 5.39 and 5.40 (overlapped singlets, 1H), 7.14 (m, 2H), 7.25–7.40 (m, 6H); MS (HR-FAB) m/z 437.0868 (M+H calcd. for C$_{21}$H$_{25}$O$_4$S$_3$ 437.0915).

Method B. A mixture of (E)-2-methyl-2-phenyl-5-[2-(3-thienyl)ethenyl]-3(2H)-furanone (40 mg, 0.14 mmol) and 1,4-dithio-DL-threitol (1.0 g, 6.4 mmol) in EtOH (4 mL) and aqueous 0.1M KH$_2$PO$_4$ pH 7.5 buffer was stirred at room temperature for 20 h. The mixture was extracted with ether and the product was purified as in Method A. or by preparative HPLC.

Method C. A mixture of (E)-2-methyl-2-phenyl-5-[2-(3-thienyl)ethenyl]-3(2H)-furanone (0.5 mg, 1.75 µmole) and 1,4-dithio-DL-threitol (47 mg, 0.3 mmol, 1M aqueous solution), DMSO (50 µL), and aqueous 0.05M Tris/HCl pH 7.5 buffer (4 mL) was stirred at room temperature for 4–20 h. After this period, 0.1% TFA in acetonitrile (0.3–0.5 mL) was added to obtain a clear solution. The latter was filtered through polypropylene (LC13 Acrodisc PVDF) and the product was purified by reverse phase HPLC.

EXAMPLE 2

5-(2-[[(2R*,3S*)-2,3-Dihydroxy-4-mercaptobutyl] thio]-2-thien-3-ylethyl)-2methyl-2-phenylfuran-3 (2H)-one Following the procedure of Method C, above, (E)-2-methyl-2-phenyl-5-[2-(3-thienyl)ethenyl]-3(2H)-furanone was reacted with 1,4-dithio-DL-erythritol to provide 5-(2-{[(2R*,3S*)-2,3-dihydroxy-4-mercaptobutyl]thio}-2-thien-3-ylethyl)-2-methyl-2-phenylfuran-3(2H)-one: $^1$H NMR (DMSO-d$_6$) δ1.53, 1.57 and 1.61 (overlapped singlets, 3H), 2.60–2.90 (m, ~4H), 3.40–3.60 (m overlapped with DMSO, ~2H), 4.60 (m, 1H), 5.52, 5.54 and 5.56 (overlapped singlets, 1H), 7.15–7.60 (m, 8H); MS (LR-ESI) m/z 437 (M+H calcd. for C$_{21}$H$_{25}$O$_4$S$_3$ 437).

EXAMPLE 3

5-[2-{[(2R,3R)-2,3-Dihydroxy-4-mercaptobutyl] thio}-2-(3-thienyl)ethyl]-2-methyl-2-phenylfuran-3 (2H)-one According to the procedure of Method A, Example 1, (E)-2-methyl-2-phenyl-5-[2-(3-thienyl)ethenyl]-3(2H)-furanone was reacted with 1,4-dithio-L-threitol to provide 5-[2-{[(2R,3R)-2,3-dihydroxy-4-mercaptobutyl]thio}-2-(3-thienyl)ethyl]-2-methyl-2-phenylfuran-3(2H)-one: $^1$H NMR (CDCL$_3$) δ1.43 (m,1H), 1.66 and 1.68 (overlapped singlets, 3H),2.40–2,70 (m,4H), 3.10–3.25 (m, 2H), 3.40–3.75 (two broad s, fine structure, 2H), 4.48 (m, 1H), 5.39 and 5.40 (overlapped singlets, 1H),7.14 (m,2H), 7.25–7.40 (m, 6H); MS (LR-??)m/z 437 (M+H calcd. for C$_{21}$H$_{25}$O$_4$S$_3$ 437); MS (HR-FAB) m/z 459.0728 (M+Na calcd. for C$_{21}$H$_{24}$NaO$_4$S$_3$ 459.0734).

EXAMPLE 4

5-(2-{[(2S*,3S*)-2,3-Dihydroxy-4-mercaptobutyl] thio}-2-thien-3-ylethyl)-2-(4-fluorophenyl)-2-methylfuran-3(2H)-one Following the procedure of Method C, Example 1, (E)-2-(4-fluorophenyl)-2-methyl-5-[2-(3-thienyl)ethenyl]-3 (2H)-furanone was reacted with 1,4-dithio-DL-threitol to give 5-(2-{[(2S*,3S*)-2,3-dihydroxy-4-mercaptobutyl] thio}-2-thien-3-ylethyl)-2-(4-fluorophenyl)-2methylfuran-3 (2H)-one: $^1$H NMR (DMSO-d$_6$) δ1.53, 1.57 and 1.60 (overlapped singlets, 3H), 4.60 (m, 1H), 5.56 and 5.57 (overlapped singlets, 1H), 7.12–7.60 (m, 7H); MS (LR-ESI) m/z 455 (M+H calcd. for C$_{21}$H$_{24}$FO$_4$S$_3$ 455).

EXAMPLE 5

5-(2-{[(2R*,3S*)-2,3-Dihydroxy-4-mercaptobutyl] thio}-2-thien-3-ylethyl)-2-(4-fluorophenyl)-2-methylfuran-3(2H)-one Following the procedure of Method C, Example 1, (E)-2-(4-fluorophenyl)-2-methyl-5-[2-(3-thienyl)ethenyl]-3 (2H)-furanone was reacted with 1,4-dithio-DLerythritol to provide 5-(2-{[(2R*,3S*)-2,3-dihydroxy-4-mercaptobutyl] thio}-2-thien-3-ylethyl)-2-(4-fluorophenyl)-2-methylfuran-3(2H)-one: $^1$H NMR (DMSO-d$_6$) δ1.53 and 1.58 (overlapped singlets, 3H), 2.65–2.85 (m, 2H), 4.57 (m, 1H), 5.54 and 5.56 (overlapped singlets, 1H), 7.12–7.60 (m, ~7H); MS (LR-ESI) m/z 455 (M+H calcd. for C$_{21}$H$_{24}$FO$_4$S$_3$ 455).

EXAMPLE 6

5-(2-{[(2R,3R)-2,3-Dihydroxy-4-mercaptobutyl] thio}-2-thien-3-ylethyl)-2-(4-fluorophenyl)-2-methylfuran-3(2H)-one According to the procedure of Method A, Example 1, (E)-2-(4-fluorophenyl)-2-methyl-5-[2-(3-thienyl)ethenyl]-3 (2H)-furanone was reacted with 1,4-dithio-L-threitol to provide 5-(2-{[(2R,3R)-2,3-dihydroxy-4-mercaptobutyl]thio}-2-thien-3-ylethyl)-2-(4-fluorophenyl)-2-methylfuran-3 (2H)-one: $^1$H NMR (CDCl$_3$) δ1.45 (m, 1H), 1.63 and 1.65 (overlapped singlets, 3H), 2.40–2.70 (m, slight xs. of 4H), 3.10–3.25 (m,2H), 3.40–3.75 (two broad s, fine structure, 2H), 4.49 (m, 1H), 5.40 and 5.41 (overlapped singlets, 1H), 7.01 (m, 2H), 7.15 (m, 2H), 7.33 (m, 3H); MS (HR-FAB) m/z 455.0818 (M+H calcd. for C$_{21}$H$_{24}$FO$_4$S$_3$ 455.0821).

EXAMPLE 7

5-[2-{[(2S*,3S*)-2,3-Dihydroxy-4-mercaptobutyl] thio}-2-(2-nitrophenyl)ethyl]-2-methyl-2-phenylfuran-3(2H)-one According to the procedure of Method A, Example 1, (E)-2-methyl-2-phenyl-5-[2-(3-thienyl)ethenyl]-3(2H)-furanone was reacted with 1,4-dithio-DL-threitol to provide 5-[2-{[(2S*,3S*)-2,3-dihydroxy-4-mercaptobutyl]thio}-2-(2-nitrophenyl)ethyl]-2-methyl-2-phenylfuran-3(2H)-one as a mixture of diastereomers: $^1$H NMR (CDCl$_3$) δ1.40 (m, 1H), 1.62, 1.67 and 1.69 (overlapped singlets, 3H), 2.50–2.75 (m, 4H), 3.17–3.38 (m,2H), 3.45–3.75 (two broad s, fine structure, 2H), 5.16 (m, 1H), 5.39, 5.40 and 5.50 (singlets, 1H), 7.25–7.50 (m, 6H), 7.65 (m, 2H); MS (LR-ESI) m/z 476 (M+H calcd. for C$_{23}$H$_{26}$NO$_6$S$_2$ 476).

EXAMPLE 8

5-(2-{[(2S*3S*)-2,3-Dihydroxy-4-mercaptobutyl] thio}-1-methyl-2-thien-3-ylethyl)-2-methyl-2-phenylfuran-3(2H)-one According to the procedure of Method A, Example 1, 2-methyl-5-[(E)-1-methyl-2-thien-3-ylethenyl]-2-phenylfuran-3(2H)-one was reacted with 1,4-dithio-DLthreitol to provide 5-(2-{[(2S*3S*)-2,3-dihydroxy-4-mercaptobutyl]thio}-1-methyl-2-thien-3-ylethyl)-2-methyl-2-phenylfuran-3(2H)-one as a mixture of diastereomers: $^1$H NMR (CDCl$_3$) δ1.45 (m, 1H), 1.50–1.65 and 1.75–1.80 (overlapped singlets and multiplets, ~8H), 2.40–2.70 (m, ~4H), 3.22 (m, 1H), 3.33–3.65 (m, 2H), 4.33 (m, 1H), 5.25–5.52 (overlapped singlets, 1H), 7.05–7.60 (m, 8H); MS (HR-FAB) m/z 451.1116 (M+H calcd. for C$_{22}$H$_{27}$O$_4$S$_3$ 451.1072).

EXAMPLE 9

5-[2-[(4-Mercaptobutyl)thio]-2-(3-thienyl)ethyl]-2-methyl-2-phenylfuran-3(2H)-one According to the procedure of Method A, Example 1, (E)-2-methyl-2-phenyl-5-[2-(3-thienyl)ethenyl]-3(2H)-furanone was reacted with 1,4-butanedithiol to provide 5-[2-[(4-mercaptobutyl)thio]-2-(3-thienyl)ethyl]-2-methyl-2-phenylfuran-3(2H)-one: $^1$H NMR (CDCl$_3$) δ1.30 (m, 1H), 1.55–1.70 (broad s with fine structure, 4H) and 1.65 and 1.68 (singlets, 3H), 2.33–2.42 (m, 2H), 2.42–2.55 (m, 2H), 3.06–3.25 (m, 2H), 4.40 (m, 1H), 5.37 and 5.39 (singlets, 1H), 7.05–7.18 (m, 2H), 7.25–7.40 (m, 6H); MS (HR-FAB) m/z 405.1029 (M+H calcd. for C$_{21}$H$_{25}$O$_2$S$_3$ 405.1017).

EXAMPLE 10

5-[2-[(4-Hydroxybutyl)thio]-2-(3-thienyl)ethyl]-2-methyl-2-phenylfuran-3(2H)-one According to the procedure of Method A, Example 1, (E)-2-methyl-2-phenyl-5-[2-(3-thienyl)ethenyl]-3(2H)-furanone was reacted with 4-mercapto-1-butanol to provide 5-[2-[(4-hydroxybutyl)thio]-2-(3-thienyl)ethyl]-2-methyl-2-phenylfuran-3(2H)-one: $^1$H NMR (CDCl$_3$) δ1.52–1.70 (broad s with fine structure, ~5H) and 1.65 and 1.67 (singlets, 3H), 2.41 (m, 2H), 3.08–3.24 (m, 2H), 3.60 (m, 2H), 4.40 (m, 1H), 5.37 and 5.39 (singlets, 1H), 7.05–7.16 (m, 2H), 7.25–7.40 (m, 6H); MS (HR-EI) m/z 388.1161 (M$^+$ calcd. for C$_{21}$H$_{24}$O$_3$S$_2$ 388.1167).

EXAMPLE 11

5-[2-[(3-Mercaptopropyl)thio]-2-(3-thienyl)ethyl]-2-methyl-2-phenylfuran-3(2H)-one According to the procedure of Method A, Example 1, (E)-2-methyl-2-phenyl-5-[2-(3-thienyl)ethenyl]-3(2H)-furanone was reacted with 1,3-propanedithiol to provide 5-[2-[(3-mercaptopropyl)thio]-2-(3-thienyl)ethyl]-2-methyl-2-phenylfuran-3(2H)-one: $^1$H NMR (CDCl$_3$) δ1.65 and 1.68 (singlets, 3H), 2.41 (m, 2H), 1.73–2.20 (overlapping multiplets, 3H), 2.45–2.65 (m, ~4H) 3.08–3.27 (m, 2H), 4.40 (m, 1H), 5.37 and 5.39 (singlets, 1H), 7.05–7.18 (m, 2H), 7.27–7.45 (m, 6H); MS (HR-FAB) m/z 391.0850 (M+H calcd. for C$_{20}$H$_{23}$O$_2$S$_3$ 391.0860).

EXAMPLE 12

5-[2-[(5-Mercaptopentyl)thio]-2-(3-thienyl)ethyl]-2-methyl-2-phenylfuran-3(2H)-one According to the procedure of Method A, Example 1, (E)-2-methyl-2-phenyl-5-[2-(3-thienyl)ethenyl]-3(2H)-furanone was reacted with 1,5-pentanedithiol to provide 5-[2-[(5-mercaptopentyl)thio]-2-(3-thienyl)ethyl]-2-methyl-2-phenylfuran-3(2H)-one: $^1$H NMR (CDCL$_3$) δ1.32 (m, 1H), 1.40–1.75 (m, 6H) and 1.65 and 1.68 (singlets, 3H), 2.33–2.45 (m, 2H), 2.45–2.60 (m, 2H), 3.06–3.25 (m, 2H), 4.40 (m, 1H), 5.37 and 5.39 (singlets, 1H), 7.05–7.18 (m, 2H), 7.25–7.43 (m, 6H); MS (HR-FAB) m/z 419.1180 (M+H calcd. for C$_{22}$H$_{27}$O$_2$S$_3$ 419.1173).

EXAMPLE 13

5-[2-[(2-Mercaptoethyl)thio]-2-(3-thienyl)ethyl]-2-methyl-2-phenylfuran-3(2H)-one According to the procedure of Method A, Example 1, (E)-2-methyl-2-phenyl-5-[2-(3-thienyl)ethenyl]-3(2H)-furanone was reacted with 1,2-ethanedithiol to provide 5-[2-[(2-mercaptoethyl)thio]-2-(3-thienyl)ethyl]-2-methyl-2-phenylfuran-3(2H)-one: $^1$H NMR (CDCl$_3$) δ1.63 (m, 1H) and overlapping 1.65 and 1.68 (singlets, 3H), 2.47–2.80 (m, 4H), 3.07–3.25 (m, 2H), 4.47 (m, 1H), 5.37 and 5.39 (singlets, 1H), 7.05–7.18 (m, 2H), 7.25–7.45 (m, 6H); MS (HR-EI) m/z 376.0605 (M$^+$ calcd. for C$_{19}$H$_{20}$O$_2$S$_3$ 376.0626).

EXAMPLE 14

5-[2-[(3-Hydroxy-2-mercaptopropyl)thio]-2-(3-thienyl)ethyl]-2-methyl-2-phenylfuran-3(2H)-one According to the procedure of Method A, Example 1, (E)-2-methyl-2-phenyl-5-[2-(3-thienyl)ethenyl]-3(2H)-furanone was reacted with 2,3-dimercapto-1-propanol to provide 5-[2-[(3-hydroxy-2-mercaptopropyl)thio]-2-(3-thienyl)ethyl]-2-methyl-2-phenylfuran-3(2H)-one: $^1$H NMR (CDCl$_3$) δ1.65 (m, 1H) and overlapping 1.65 and 1.68 (singlets, 3H), 1.92 (br s with fine structure, 1H), 2.65–2.80 (m, 2H), 2.89 (br s with fine structure, 1H), 3.10–3.28 (m, 2H), 4.43–4.60 (m, 1H), 5.38, 5.40 and 5.41 (singlets, 1H), 7.13–7.20 (m, 2H), 7.25–7.43 (m, 6H); MS (LR-ESI) m/z 407 (M+H calcd. for C$_{20}$H$_{23}$NO$_3$S$_3$ 407).

EXAMPLE 15

5-[2-[(3-Hydroxypropyl)thio]-2-(3-thienyl)ethyl]-2-methyl-2-phenylfuran-3(2H)-one According to the procedure of Method A, Example 1, (E)-2-methyl-2-phenyl-5-[2-(3-thienyl)ethenyl]-3(2H)-furanone was reacted with 3-mercapto-1-propanol to provide 5-[2-[(3-hydroxypropyl)thio]-2-(3-thienyl)ethyl]-2-methyl-2-phenylfuran-3(2H)-one; $^1$H NMR (CDCl$_3$) δ1.40 (br s, 1H), 1.65 and 1.68 (singlets, 3H), 1.68–1.82 (m, 2H), 2.42–2.57 (m, 2H), 3.10–3.27 (m, 2H), 3.67 (m, 2H), 4.42 (m, 1H), 5.37 and 5.39 (singlets, 1H), 7.05–7.18 (m, 2H), 7.27–7.40 (m, 6H); MS (HR-FAB) m/z 375.1113 (M+H calcd. for C$_{20}$H$_{23}$O$_3$S$_2$ 375.1089).

EXAMPLE 16

5-[2-[(2,3-Dihydroxypropyl)thio]-2-(3-thienyl)ethyl]-2-methyl-2-phenylfuran-3(2H)-one According to the procedure of Method A, Example 1, (E)-2-methyl-2-phenyl-5-[2-(3-thienyl)ethenyl]-3(2H)-furanone was reacted with 3-mercapto-1,2-propanediol to provide 5-[2-[(2,3-dihydroxypropyl)thio]-2-(3-thienyl)ethyl]-2-methyl-2-phenylfuran-3(2H)-one; $^1$H NMR (CDCl$_3$) δ1.66 and 1.68 (singlets, 3H), 1.83 (br s, 1H), 2.44 (br s with fine structure, 1H) and overlapping 2.45–2.58 (m, 2H), 3.10–3.28 (m, 2H), 3.47 (br s with fine structure, 1H), 3.55–3.78 (m, 2H), 4.50 (m, 1H), 5.39 and 5.40 (overlapping singlets, 1H), 7.05–7.20 (m, 2H), 7.27–7.43 (m, 6H); MS (HR-EI) m/z 390.0948 (M$^+$ calcd. for C$_{20}$H$_{22}$O$_4$S$_2$ 390.0959).

EXAMPLE 17

2-Methyl-2-phenyl-5-[2-[(2-pyrazin-2-ylethyl)thio]-2-(3-thienyl)ethyl]furan-3(2H)-one According to the procedure of Method A, Example 1,(E)-2-methyl-2-phenyl-5-[2-(3-thienyl)ethenyl]-3(2H)-furanone was reacted with 2-(2-mercaptoethyl)pyrazine to provide 2-methyl-2-phenyl-5-[2-[(2-pyrazin-2-ylethyl)thio]-2-(3-thienyl)ethyl]furan-3(2H)-one: $^1$H NMR (CDCl$_3$) δ1.64 and 1.65 (singlets, 3H), 2.75–2.87 (m, 2H), 2.87–2.98 (m, 2H), 3.07–3.24 (m, 2H), 4.41 (m, 1H), 5.34 and 5.36 (singlets, 1H), 7.03–7.17 (m, 2H), 7.27–7.41 (m, 6H), 8.36 (m, 1H), 8.41 (m, 1H) 8.47 (m, 1H); MS (HR-EI) m/z 422.1118 (M$^+$ calcd. for C$_{23}$H$_{22}$N$_2$O$_2$S$_2$ 422.1122).

EXAMPLE 18

5-[2-[(2-Hydroxyethyl)thio]-2-(3-thienyl)ethyl]-2-phenylfuran-3(2H)-one

Following the procedure of Method C, Example 1, (E)-2-methyl-2-phenyl-5-[2-(3-thienyl)ethenyl]-3(2H)-furanone was reacted with 2-mercapto-1-ethanol to provide 5-[2-[(2-hydroxyethyl)thio]-2-(3-thienyl)ethyl]-2-methyl-2-phenylfuran-3(2H)-one: $^1$H NMR (DMSO-d$_6$) δ1.54 and 1.57 (singlets, 3H), 3.35–3.60 (m ovelapped with DMSO, ~4H), 4.58 (m, 1H), 5.55 and 5.56 (overlapped singlets, 1H), 7.18–7.37 (m, 6H), 7.40–7.57 (m, 2H); MS(LR-ESI) m/z 361 (M+H calcd. for C$_{19}$H$_{21}$O$_3$S$_2$ 361).

EXAMPLE 19

2-(4-Fluorophenyl)-5-[2-[(2-hydroxyethyl)thio]-2-(3-thienyl)ethyl]-2-methylfuran-3(2H)-one Following the procedure of Method C, Example 1, (E)-2-(4-fluorophenyl)-2-methyl-5-[2-(3-thienyl)ethenyl]-3(2H)-furanone was reacted with 2-mercapto-1-ethanol to provide 2-(4-fluorophenyl)-5-[2-[(2-hydroxyethyl)thio]-2-(3-thienyl)ethyl]-2-methylfuran-3(2H)-one: $^1$H NMR (DMSO-d$_6$) δ1.53 and 1.56 (singlets, 3H), 4.39 (m, 1H), 5.56 (overlapped singlets, 1H), 7.08–7.35 (m, 5H), 7.43–7.60 (m, 2H); MS (HR-Cl) m/z 379.0832 (M+H calcd. for C$_{19}$H$_{20}$FO$_3$S$_2$ 379.0837)

EXAMPLE 20

(2R)-2-Amino-3-{[2-(5-methyl-4-oxo-5-phenyl-4,5-dihydrofuran-2-yl)-1-thien-3-ylethyl]thio}propanoic acid Following the procedure of Method C, Example 1, (E)-2-methyl-2-phenyl-5-[2-(3-thienyl)ethenyl]-3(2H)-furanone was reacted with L-cysteine to provide (2R)-2-amino-3-{[2-(5-methyl-4-oxo-5-phenyl-4,5-dihydrofuran-2yl)-1-thien-3-ylethyl]thio}propanoic acid: $^1$H NMR (DMSO-d$_6$) δ1.50–1.60 (overlapping singlets, 3H), 2.70–3.10 (m, ~2H), 4.00–4.25 (m, 1H), 4.64 (m, 1H), 5.50–5.57 (overlapping singlets, 1H), 7.12–7.38 (m, 6H), 7.52–7.63 (m, 2H), 8.35 (br s, ~2H); MS (LR-ESI) m/z 402 (M-H calcd. for C$_{20}$H$_{20}$NO$_4$S$_2$ 402)

What is claimed is:

1. A compound of Formula (I)

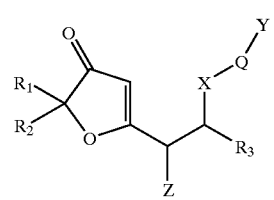

Formula (I)

wherein:

R$_1$ is alkyl of 1 to 10 carbon atoms optionally substituted with 1 to 4 substituents independently selected from the group consisting of alkyl of 1 to 10 carbon atoms, —OH, —SH, —NH, and holgen, alkenyl of 2 to 12 carbon atoms, optionally substituted aralkyl of 7 to 13 carbon atoms, optionally substituted aryl of 6 to 12 carbon atoms, and optionally substituted heteroaryl;

R$_2$ is phenyl, substituted phenyl (having from 1 to 3 substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms) or naphthyl;

R$_3$ is optionally substituted aryl and optionally substituted heteroaryl;

X is —O—, —S—, or —NH;

Y is —OH, —SH$_4$, —NH$_2$, —NHR$_5$, —CO$_2$H, —CONHOH, halogen, or heteroaryl;

R$_4$ is hydrogen, alkyl of 1 to 10 carbon atoms, aryl of 6 to 12 carbon atoms, and aralkyl of 7 to 13 carbon atoms;

R$_5$ is alkyl of 1 to 10 carbond atoms, aryl of 6 to 12 carbon atoms, and aralkyl of 7 to 13 carbon atoms;

Z is H or methyl;

Q is an alkyl chain of 2 to 6 carbon atoms optionally substituted with 1 to 4 substituents independently selected from the group consisting of alkyl of 1 to 10 carbon atoms, —OH, —SH, —NH, halogen and alkenyl of 2 to 6 carbon atoms;

or a pharmacologically acceptable salt thereof.

2. A compound according to claim 1 wherein X is S or a pharmaceutically acceptable salt thereof.

3. A compound according to claim 1 wherein X is S and Y is SH or a pharmaceutically acceptable salt thereof.

4. A compound according to claim 1 wherein X is S; Y is SH and R$_3$ is thienyl or a pharmaceutically acceptable salt thereof.

5. A compound according to claim 1 wherein X is S; Y is selected from the group consisting of SH, tetrazole and imidazole and R$_3$ is thienyl or a pharmaceutically acceptable salt thereof.

6. A compound according to claim 1 wherein X is S; Y is SH;

R$_2$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms; and R₃ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoralkyl of 1 to 10 carbon atoms, and alkoxy of 1 to 10 carbon atoms or a pharmaceutically acceptable salt thereof.

7. A compound according to claim 1 wherein X is S;

$R_1$ is methyl;

$R_2$ is phenyl optionally substituted with one to three substituentyl each independently selected from the group consisting of halogen, alkyl of 1 to 10 carbon atoms alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms when $R_3$ is thienyl and Y is SH or a pharmaceutically acceptable salt thereof.

8. A compound according to claim 1 wherein X is S;

$R_1$ is methyl;

$R_2$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoralkyl of 1 to 10 carbon atoms, and alkoxy of 1 to 10 carbon atoms when $R_3$ is thienyl and Y is pyrazine or a pharmaceutically acceptable salt thereof.

9. A compound according to claim 1 wherein X is S;

$R_1$ is methyl;

$R_2$ is phenyl optionally substituted with one to three substituents each independently selected from the group consisting os halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms;

$R_3$ phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms when Y is SH or a pharmaceutically acceptable salt thereof.

10. The compound of claim 1, wherein the compound is selected from the group consisting of 5-(2-{[(2S*,3S*)-2,3-dihydroxy-4-mercaptobutyl]thio}-2-thien-3-ylethyl)-2-methyl-2-phenylfuran-3(2H)-one, 5-(2-{[(2R*,3R*)-2,3-dihydroxy-4-mercaptobutyl]thio}-2-thien-3-ylethyl)-2-methyl-2-phenylfuran-3(2H)-one, 5-[2-{[(2R,3R)-2,3-dihydroxy-4-mercaptobutyl]thio}-2(3-thienyl)ethyl]-2-methyl-2-phenylfuran-3(2H)-one, 5-(2-{[(2S*,3S*)-2,3-dihydroxy-4-mercaptobutyl]thio}-2-thien-3-ylethyl)-2-(4-fluorophenyl)-2-methylfuran-3(2H)-one, 5-(2-{[(2R*,3R*)-2,3-dihydroxy-4-mercaptobutyl]thio}-2-thien-3-ylethyl-2(4-fluorophenyl)-2-methylfuran-3(2H)-one, 5-(2-{[(2R,3R)-2,3-dihydroxy-4-mercaptobutyl]thio}-2-thien-3-ylethyl)-2-(4-fluorophenyl)-2-methylfuran-3(2H)-one, 5-[2-{[(2S*,3S*)-2,3-dihydroxy-4-mercaptobutyl]thio}-2-(2-nitrophenyl)ethyl]-2-methyl-2-phenylfuran-3(2H)-one, 5-(2-{[(2S*,3S*)-2,3-dihydroxy-4-mercaptobutyl]thio}-1-methyl-2-thien-3ythethl)-2-methyl-2-phenylfuran-3(2H)-one, 5-[2-(4-Mecapto-butylthio)-2-thiophen-3-yl-ethyl]-2-methyl-2phenylfuran-3-one, 5-[2-[(4-hydroxybutyl)thio]-2-(3-thienyl)ethyl]-2-methyl-2-phenylfuran-3(2H)-one, 5-[2-[(3-mercaptopropyl)thio]-2-(3-thienyl)ethyl]-2-methyl-2-phenylfuran-3(2H)-one, 5-[2-[(5-mercaptopentyl)thio]-2-(3-thienyl)ethyl]-2-methyl-2-phenylfuran-3(2H)-one, 5-[2-[(2-mercaptoethyl)thio]-2-(3-thienyl)ethyl]-2-methyl-2-phenylfuran-3(2H)-one, 5-[2-[(3-hydroxy-2-mercaptopropyl)thio]-2-(3thienyl)ethyl]-2-methyl-2-phenylfuran-3(2H)-one, 5-[2-[(3-hydroxypropyl)thio]-2-(3-thienyl)ethyl]-2-methyl-2-phenylfuran-3(2H)-one, 5-[2-[(2,3-dihydroxypropyl)thio]-2-(3-thienyl)ethyl]-2-methyl-2-phenylfuran-3(2H)-one, 2-methyl-2-phenyl-5-[2-[(2-pyrazin-2-ylethyl)thio]-2-(3-thienyl)ethyl]furan-3(2H)-one, 5-[2-[(2-hydroxyethyl)thio]-2-(3-thienyl)ethyl]-2-phenylfuran-3(2H)-one, 2-(4-fluorophenyl)-5-[2-[(2-hydroxyethyl)thio]-2-(3-thienyl)ethyl]-2-methylfuran-3(2H)-one, and (2R)-2-amino-3-{[2-(5-methyl-4-oxo-5-phenyl-4,5-dihydrofuran-2-yl)-1-thien-3-ylethyl]thio}propanoic acid or a pharmaceutically acceptable salt thereof.

11. a pharmaceutical composition comprising an effective amount of a compound of claim 1 in combination with one or more pharmaceutically acceptable carriers.

12. A pharmaceutical composition according to claim 11 wherein X is S or a pharmaceutically acceptable salt thereof.

13. A pharmaceutical composition according to claim 11 wherein X is S and Y is SH or a pharmaceutically acceptable salt thereof.

14. A pharmaceutical composition according to claim 11 wherein X is S; Y is SH and $R_3$ is thienyl or a pharmaceutically acceptable salt thereof.

15. A pharmaceutical composition according to claim 11 wherein X is S; Y is selected from the group consisting of SH, tetrazole and imidazole and $R_3$ is thienyl or a pharmaceutically acceptable salt thereof.

16. A pharmaceutical composition according to claim 11 wherein X is S; Y is SH;

$R_2$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms; and $R_3$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms or a pharmaceutically acceptable salt thereof.

17. A pharmaceutical composition according to claim 11 wherein X is S;

$R_1$ is methyl;

$R_2$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms when $R_3$ is thienyl and Y is SH or a pharmaceutically acceptable salt thereof.

18. A pharmaceutical composition according to claim 11 wherein X is S; $R_1$ is methyl;

$R_2$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms when $R_3$ is thienyl and Y is pyrazine or a pharmaceutically acceptable salt thereof.

19. A pharmaceutical composition according to claim 11 wherein X is S;

$R_1$ is methyl;

$R_2$ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms;

$R_3$ is phenyl optionally substituted with one to three substituents each independently selected from the group consisting of halogen, alkyl of 1 to 10 carbon atoms, alkylthio of 1 to 10 carbon atoms, alkylamino of 1 to 10 amino, carboxy, alkylsulfonyl of 1 to 10 carbon atoms, cyano, nitro, perfluoroalkyl of 1 to 10 carbon atoms, and alkoxy of 1 to 10 carbon atoms when Y is SH or a pharmaceutically acceptable salt thereof.

20. A pharmaceutical composition according to claim 11, wherein the compound is selected from the group consisting of 5-(2-{[(2S*,3S*)-2,3-dihydroxy-4-mercaptobutyl]thio}-2-thien-3-ylethyl)-2-methyl-2-phenylfuran-3(2H)-one, 5-(2-{[(2R*,3S*)-2,3-dihydroxy-4-mercaptobutyl]thio}-2-thien-3-ylethyl)-2-methyl-2-phenylfuran-3(2H)-one, 5-[2-{[(2R,3R)-2,3-dihydroxy-4-mercaptobutyl]thio}-2-(3-thienyl)ethyl]-2-methyl-2phenylfuran-3(2H)-one, 5-(2-{[(2S*,3S*)-2,3-dihydroxy-4-mercaptobutyl]thio}-2-thien-3-ylethyl)-2-(4-fluorophenyl)-2-methylfuran-3(2H)-one, 5-(2-{[(2R*,3S*)-2,3-dihydroxy-4-mercaptobutyl]thio}-2-thien-3-ylethyl)-2-(4-fluorophenyl)-2-methylfuran-3(2H)-one, 5-(2-{[(2R,3R)-2,3-dihydroxy-4-mercaptobutyl]thio}-2-thien-3-ylethyl)-2-(4-fluorophenyl)-2-methylfuran-3(2H)-one, 5-[2-{[(2S*,3S*)-2,3-dihydroxy-4-mercaptobutyl]}-2-(2-nitrophenyl)ethyl]-2-methyl-2-phenylfuran-3(2H)-one, 5-(2-{[(2S*,3S*)-2,3-dihydroxy-4-mercaptobutyl]thio}-1-methyl-2-thien-3-ylethyl)-2-methyl-2-phenylfuran-3(2H)-one, 5-[2-(4-Mercapto-butylthio)-2thiophen-3-yl-ethyl]-2-methyl-2-phenylfuran-3-one, 5-[2-[(4-hydroxybutyl)thio]-2-(3-thienyl)ethyl]-2-methyl-2-phenylfuran-3(2H)-one, 5-[2-[(3-mercaptopropyl)thio]-2-(3-thienyl)ethyl]-2-methyl-2-phenylfuran-3(2H)-one, 5-[2-[(5-mercaptopentyl)thio]-2-(3-thienyl)ethyl]-2-methyl-2-phenylfuran-3(2H)-one, 5-[2-[(2-mercaptoethyl)thio]-2-(3-thienyl)ethyl]-2-methyl-2-phenylfuran-3(2H)-one, 5-[2-[(3-hydroxy-2-mercaptopropyl)thio]-2-(3-thienyl)ethyl]-2-methyl-2-phenylfuran-3(2H)-one, 5-[2-[(3-hydroxypropyl)thio]-2-(3-thienyl)ethyl]-2-methyl-2-phenylfuran-3(2H)-one, 5-[2-[(2,3-dihydroxypropyl)thio]-2-(3-thienyl)ethyl]-2-methyl-2-phenylfuran-3(2H)-one, 2-methyl-2-phenyl-5-[2-[(2-pyrazin-2-ylethyl)thio]-2-(3-thienyl)ethyl]furan-3(2H)-one, 5-[2-[(2-hydroxyethyl)thio]-2-(3-thienyl)ethyl]-2-methyl-2-phenylfuran-3(2H)-one, 2-(4-fluorophenyl)-5-[2-[(2-hydroxyethyl)thio]-2-(3-thienyl)ethyl]-2-methylfuran-3(2H)-one, and (2R)-2-amino-3-{[2-(5-methyl-4-oxo-5-phenyl-4,5-dihydrofuran-2-yl)-1-thien-3-ylethyl]thio}propanoic acid or a pharmaceutically acceptable salt thereof.

21. A method of treating, inhibiting or controlling a ras-associated disease by inhibiting farnesyl-protein transferase (FPTase) enzyme in a mammal in need thereof, which comprises administering to said mammal an effective amount of a compound of Formula (I)

Formula (I)

wherein:

$R_1$ is alkyl of 1 to 10 carbon atoms optionally substituted with 1 to 4 substituents selected from the group consisting of alkyl of 1 to 10 carbon atoms, —OH, —SH, —NH, and halogen, alkenyl of 2 to 12 carbon atoms, optionally substituted aralkyl of 7 to 13 carbon atoms, optionally substituted aryl of 6 to 12 carbon atoms, and optionally substituted heteroaryl;

$R_2$ is phenyl, substituted phenyl (having from 1 to 3 substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms) or naphthyl;

$R_3$ is optionally substituted aryl and optionally substituted heteroaryl;

X is —O—, —S—, or —NH;

Y is —OH, —SH, —$SR_4$, —$NH_2$, —$NHR_5$, —$CO_2H$, —CONHOH, halogen, or heteroaryl;

$R_4$ is hydrogen, alkyl 1 to 10 carbon atoms, aryl of 6 to 12 carbon atoms, and aralkyl of 7 to 13 carbon atoms;

$R_5$ is alkyl of 1 to 10 carbon atoms, aryl of 6 to 12 carbon atoms, and aralkyl of 7 to 13 carbon atoms;

Z is H or methyl;

Q is an alkyl chain of 2 to 6 carbon atoms optionally substituted with 1 to 4 substituents selected from the group consisting of alkyl of 1 to 10 carbon atoms, —OH, —SH, —NH, halogen and alkenyl of 2 to 6 carbon atoms;

or a pharmacologically acceptable salt thereof.

22. The method according to claim 21 wherein X is S or a pharmaceutically acceptable salt thereof.

23. The method according to claim 21 wherein X is S and Y is SH or a pharmaceutically acceptable salt thereof.

24. The method according to claim 21 wherein X is S; Y is SH and R₃ is thienyl or a pharmaceutically acceptable salt thereof.

25. The method according to claim 21 wherein X is S; Y is selected from the group consisting of SH, tetrazole and imidazole and R₃ is thienyl or a pharmaceutically acceptable salt thereof.

26. The method according to claim 21 wherein X is S; Y is SH;

R₂ phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms; and R₃ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms or a pharmaceutically acceptable salt thereof.

27. The method according to claim 21 wherein X is S; R₁ is methyl;

R₂ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms when R₃ is thienyl and Y is SH or a pharmaceutically acceptable salt thereof.

28. The method according to claim 21 wherein X is S; R₁ is methyl;

R₂ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms when R₃ is thienyl and Y is pyrazine or a pharmaceutically acceptable salt thereof.

29. The method according to claim 21 wherein X is S; R₁ is methyl;

R₂ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms;

R₃ is phenyl optionally substituted with one to three substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms when Y is SH or a pharmaceutically acceptable salt thereof.

30. The method of claim 21, wherein the compound is selected from the group consisting of 5-(2{[(2S*,3S*)-2,3-dihydroxy-4-mercaptobutyl]thio}-2-thien-3-ylethyl)-2-methyl-2-phenylfuran-3(2H)-one, 5-(2-{[(2R*,3S*)-2,3-dihydroxy-4-mercaptobutyl]thio}-2-thien-3-ylethyl)-2-methyl-2-phenylfuran-3(2H)-one, 5-2-{[(2R,3R)-2,3-dihydroxy-4-mercaptobutyl]thio}-2-(3-thienyl)ethyl]-2-methyl-2-phenylfuran-3(2H)-one, 5-(2-{[(2S*,3S*)-2,3-dihydroxy-4-mercaptobutyl]thio}-2-thien-3-ylethyl)-2-(4-fluorophenyl)-2-methylfuran-3(2H)-one, 5-(2-{[(2R*,3S*)-2,3-dihydroxy-4-mercaptobutyl]thio}-2-thien-3-ylethyl)-2-(4-fluorophenyl)-2-methylfuran-3(2H)-one, 5-(2-{[(2R,3R)-2,3-dihydroxy-4-mercaptobutyl]thio}-2-thien-3-ylethyl)-2-(4-fluorophenyl)-2-methylfuran-3(2H)-one, 5-[2-{[(2S*,3S*)-2,3-dihydroxy-4-mercaptobutyl]thio}-2-(2-nitrophenyl)ethyl]-2-methyl-2-phenylfuran-3(2H)-one, 5-(2-{[(2S*,3S*)-2,3-dihydroxy-4-mercaptobutyl]thio}-1-methyl-2-thien-3-ylethyl)-2-methyl-2-phenylfuran-3(2H)-one, 5-[2-(4-Mercapto-butylthio)-2-thiophen-3-yl-ethyl]-2-methyl-2-phenylfuran-3-one, 5-[2-[(4-hydroxybutyl)thio]-2-(3-thienyl)ethyl]-2-methyl-2-phenylfuran-3(2H)-one, 5-[2-[(3-mercaptopropyl)thio]-2-(3-thienyl)ethyl]-2-methyl-2-phenylfuran-3(2H)-one, 5-[2-[(5-mercaptopentyl)thio]-2-(3-thienyl)ethyl]-2-methyl-2-phenylfuran-3(2H)-one, 5-[2-[(2-mercaptoethyl)thio]-2-(3-thienyl)ethyl]-2-methyl-2-phenylfuran-3(2H)-one, 5-[2-[(3-hydroxy-2-mercaptopropyl)thio]-2-(3-thienyl-ethyl]-2-methyl-2-phenylfuran-3(2H)-one, 5-[2-[(3-hydroxypropyl)thio]-2-(3-thienyl)ethyl]-2-methyl-2-phenylfuran-3(2H)-one, 5-[2-[(2,3-dihydroxypropyl)thio]-2-(3-thienyl)ethyl]-2-methyl-2-phenylfuran-3(2H)-one, 2-methyl-2-phenyl-5-[2-[(2-pyrazin-2-ylethyl)thio]-2-(3-thienyl)ethyl]furan-3(2H)-one, 5-[2-[(2-hydroxyethyl)thio]-2-(3-thienyl)ethyl]-2-methyl-2-phenylfuran-3(2)-one, 2-(4-fluorophenyl)-5-[2-[(2-hydroxyethyl)thio]-2-(3-thienyl)ethyl]-2-methylfuran-3(2H)-one, and (2R)-2-amino-3-{[2-(5-methyl-4-oxo-5-phenyl-4,5-dihydrofuran-2-yl)-1-thien-3-ylethyl]thio}propanoic acid or a pharmaceutically acceptable salt thereof.

31. The method of claim 21 wherein the ras-associated disease in mammals is selected from the group consisting of cancers of the pancreas, breast, lung, colon, epidermis, prostate, bladder, thyroid, myelodysplastic tumors and myeloid leukemia.

32. The method of claim 21 wherein the ras-associated disease in mammals is selected from metastasis, suppressing angiogenesis, and inducing apoptosis.

33. The method of claim 21 wherein the ras-associated proliferative disease in mammals is restenosis, neurofibromatosis, endometriosis, and psoriasis.

34. The method of claim 21 wherein the ras-associated disease in mammals is prenyl modifications or proteins.

35. A process for the preparation of a compound of Formula (I):

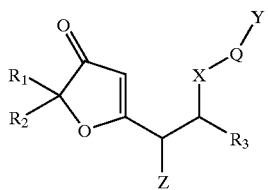

Formula (I)

wherein:
- R₁ is alkyl of 1 to 10 carbon atoms optionally substituted with 1 to 4 substituents selected from the group consisting of alkyl of 1 to 10 carbon atoms, —OH, —SH, —NH₂, and halogen, alkenyl of 2 to 12 carbon atoms, optionally substituted aralkyl of 7 to 13 carbon atoms, optionally substituted aryl of 6 to 12 carbon atoms, and optionally substituted hereroaryl;
- R₂ is phenyl, substituted pheyl (having 1 to 3 substituents each independently selected from the group consisting of halogen, alkyl of 1 to 10 carbon atoms, alkylthio of 1 to 10 carbon atoms, alkylamino of 1 to 10 carbon atoms, amino, carboxy, alkylsulfonyl of 1 to 10 carbon atoms, cyano, nitro, perfluoroalkyl of 1 to 10 carbon atoms, and alkoxy of 1 to 10 carbon atoms), or naphthyl;
- R₃ is optionally substituted aryl and optionally substituted heteroaryl;
- X is —O—, —S—, or —NH—;
- Y is —OH, —SH, —SR₄, —NH₂, —NHR₅, —CO₂H, —CONHOH, halogen, or heteroaryl;
- R₄ is hydrogen, alkyl of 1 to 10 carbon atoms, aryl of 6 to 12 carbon atoms, and aralkyl of 7 to 13 carbon atoms;
- R₅ is alkyl of 1 to 10 carbon atoms, aryl of 6 to 12 carbon atoms, and aralkyl of 7 to 13 carbon atoms;
- Z is H or methyl;
- Q is an alkyl chain of 2 to 6 carbon atoms optionally substituted with 1 to 4 substituents selected from the group consisting of alkyl of 1 to 10 carbon atoms, —OH, —SH, —NH₂, halogen and alkenyl of 2 to 6 carbon atoms;

or a pharmacologically acceptable salt thereof which comprises (a) reacting a compound of formula

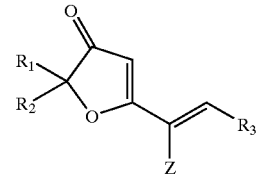

with a compound of the formula HX—Q—Y to give a compound of Formula (I);

(b) optionally converting a compound of Formula (I) to a pharmaceutically acceptable salt thereof.

36. A process according to claim 35 in the presence of triethylamine in tetrahydrofuran.

37. A process according to claim 35 in the presence of aqueous phosphate buffer.

38. A process according to claim 35 in the presence of tris(hydroxymethyl)aminomethane hydrochloride in dimethylsulfoxide.

* * * * *